(12) United States Patent
Gupta et al.

(10) Patent No.: US 9,408,543 B1
(45) Date of Patent: Aug. 9, 2016

(54) NON-INVASIVE METHOD AND SYSTEM FOR CHARACTERIZING CARDIOVASCULAR SYSTEMS FOR ALL-CAUSE MORTALITY AND SUDDEN CARDIAC DEATH RISK

(71) Applicant: Analytics For Life, Ganaoque (CA)

(72) Inventors: Sunny Gupta, Amherstview (CA); Mohsen Najafi Yazdi, Kingston (CA); Timothy William Fawcett Burton, Ottawa (CA); Shyamlal Ramchandani, Kingston (CA); Derek Vincent Exner, Calgary (CA)

(73) Assignee: Analytics For Life, Ganaoque, Ontario (CA)

( * ) Notice: Subject to any disclaimer, the term of this patent is extended or adjusted under 35 U.S.C. 154(b) by 0 days.

(21) Appl. No.: 13/970,582

(22) Filed: Aug. 19, 2013

Related U.S. Application Data

(60) Provisional application No. 61/684,282, filed on Aug. 17, 2012.

(51) Int. Cl.
*A61B 5/00* (2006.01)
*A61B 5/04* (2006.01)
(Continued)

(52) U.S. Cl.
CPC ............ *A61B 5/04012* (2013.01); *A61B 5/021* (2013.01); *A61B 5/0205* (2013.01); *A61B 5/029* (2013.01); *A61B 5/044* (2013.01);
(Continued)

(58) Field of Classification Search
CPC .................................. A61B 5/04011
USPC ................................ 600/512, 485
See application file for complete search history.

(56) References Cited

U.S. PATENT DOCUMENTS

| | | | |
|---|---|---|---|
| 6,325,761 B1 * | 12/2001 | Jay | 600/485 |
| 2009/0312648 A1 | 12/2009 | Zhang et al. | |
| 2011/0087121 A1 | 4/2011 | Zhang et al. | |
| 2014/0309707 A1 | 10/2014 | Marculescu | |

FOREIGN PATENT DOCUMENTS

WO       2012/106729       8/2012

OTHER PUBLICATIONS

Benmalek, M., et al., "Digital fractional order operators for R-wave detection in electrocardiogram signal," IET Signal Processing, vol. 3, Issue 5, 2009, pp. 381-391.

(Continued)

*Primary Examiner* — Theodore Stigell
*Assistant Examiner* — Nadia A Mahmood
(74) *Attorney, Agent, or Firm* — Meunier Carlin & Curfman LLC

(57) ABSTRACT

Methods and systems for evaluating the electrical activity of the heart to identify novel ECG patterns closely linked to the subsequent development of serious heart rhythm disturbances and fatal cardiac events. Two approaches are describe, for example a model-based analysis and space-time analysis, which are used to study the dynamical and geometrical properties of the ECG data. In the first a model is derived using a modified Matching Pursuit (MMP) algorithm. Various metrics and subspaces are extracted to characterize the risk for serious heart rhythm disturbances, sudden cardiac death, other modes of death, and all-cause mortality linked to different electrical abnormalities of the heart. In the second method, space-time domain is divided into a number of regions (e.g., 12 regions), the density of the ECG signal is computed in each region and input to a learning algorithm to associate them with these events.

19 Claims, 19 Drawing Sheets

(51) Int. Cl.
  *A61B 5/0205*  (2006.01)
  *A61B 5/021*  (2006.01)
  *A61B 5/029*  (2006.01)
  *A61B 5/044*  (2006.01)
  *A61B 5/0468*  (2006.01)
  *A61B 5/1455*  (2006.01)

(52) U.S. Cl.
  CPC ........... *A61B5/04011* (2013.01); *A61B 5/0468* (2013.01); *A61B 5/14551* (2013.01); *A61B 5/4836* (2013.01)

(56) References Cited

OTHER PUBLICATIONS

Exner, D.V., et al., "Noninvasive Risk Assessment Early After a Myocardial Infarction," The Refine Study, Journal of the American College of Cardiology, vol. 50, No. 24, 2007, pp. 2275-2284.

Mallat, S.G., et al., "Matching Pursuits with Time-Frequency Dictionaries," IEEE Transactions on Signal Processing, vol. 41, No. 12, 1993, pp. 3397-3415.

* cited by examiner

Blinded analysis of left ventricular ejection fraction, heart rate turbulence slope and T wave alternans voltage combined as continuous measures to predict the risk of cardiac death or resuscitated cardiac arrest (N = 303).

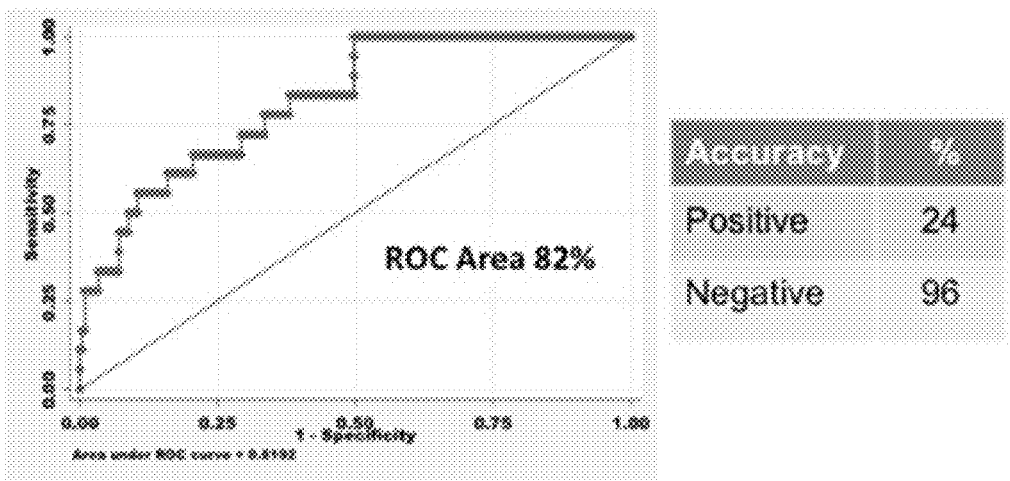

Blinded analysis of the proposed risk assessment approach presented as a ranking of patients to predict the risk of cardiac death or resuscitated cardiac arrest (N = 289).

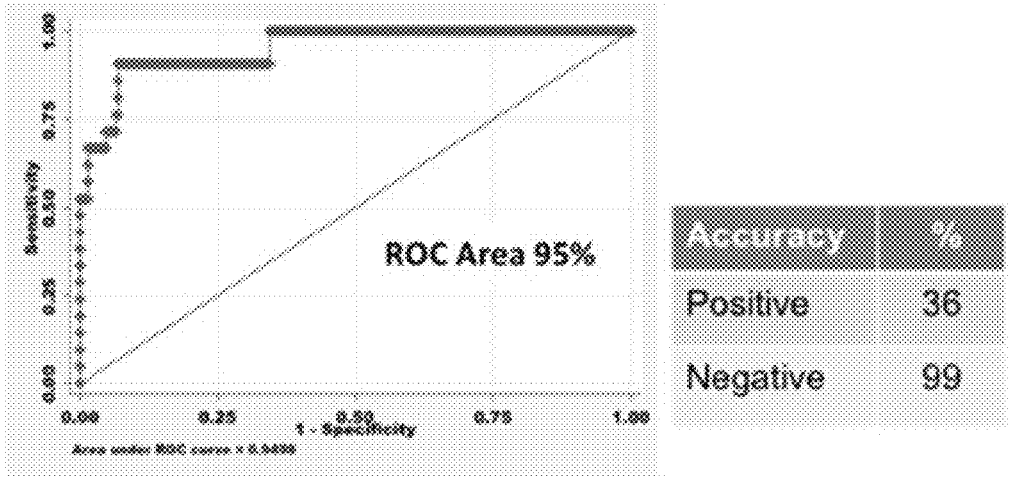

FIG. 10

Alteration in left ventricular morphology score at baseline as compared to 12 months of treatment with placebo (N = 6) versus atorvastatin (N = 6).

|  | | Groups | | |
|---|---|---|---|---|
|  | | Overall (N = 12) | Placebo (N = 6) | Atorvastatin (N = 6) |
| Morphology Score | Baseline | 3.0 ± 1.4 | 2.7 ± 1.0 | 3.2 ± 1.6 |
| | 12 months | 1.9 ± 1.0 | 2.5 ± 0.8 | 1.3 ± 0.6 |
| | Change | - 1.1 ± 1.3 | - 0.2 ± 0.7 | - 1.9 ± 1.2 |
| T-test p-value | | 0.02 | 0.6 | 0.009 |
| Wilcoxon p-value | | 0.02 | 0.9 | 0.03 |

Data presented as mean ± standard deviation

*FIG. 12*

Non-Invasive Assessment of patient response to therapy

- 48 year old male presented with symptomatic, new onset Atrial fibrilation. He converted to normal sinus rhythm on Diltiazem and Dronaderone.
- Echocardiography showed left atrial enlargement and abnormal flow near the atrial myocardium.
- A4L CardioAnalysis of ECG shows interesting results in the presence and absence of medications.

| Off Medication | On Medication |
|---|---|
| Atrial Stability Risk Score = 0.2012 | Atrial Stability Risk Score = 0.0253 |

*FIG. 13*

NON-INVASIVE METHOD AND SYSTEM FOR CHARACTERIZING CARDIOVASCULAR SYSTEMS FOR ALL-CAUSE MORTALITY AND SUDDEN CARDIAC DEATH RISK

CROSS-REFERENCE TO RELATED APPLICATION

This application claims priority to U.S. Provisional Patent Application No. 61/684,282, filed on Aug. 17, 2012, entitled "NON-INVASIVE METHOD AND SYSTEM FOR CHARACTERIZING CARDIOVASCULAR SYSTEMS FOR ALL-CAUSE MORTALITY AND SUDDEN CARDIAC DEATH RISK," which is incorporated herein by reference in its entirety.

BACKGROUND

Present methods employed to assess cardiac and other physiological signals are typically rudimentary. It is claimed that prior methods can be improved upon via techniques that identify novel ECG patterns using advanced mathematical techniques that assess dynamic alterations in cardiac conduction and repolarization along with alterations in vascular and autonomic function. The surface ECG contains information on the electrical properties of the heart and represents the sum of electrical activity of the heart, along with vascular and autonomic nervous system dynamics. Moreover, cardiac electrical activity directly relates to cardiac architecture and alterations in cardiac architecture are detectable on a surface ECG. The challenges are to winnow out information related to abnormalities in cardiac conduction and repolarization, cardiac architecture, along with vascular and autonomic function from noise and other artifacts and to identify novel ECG patterns that reliably predict the development of serious heart rhythm disturbances, sudden cardiac death, other modes of death and all-cause mortality.

Prior ECG-based methods to identify patients at risk of sudden death and mortality are not sufficiently accurate. Even the best techniques have areas under the receiver operating characteristic curve of 0.80 or less in predicting the development of serious heart rhythm disturbances, sudden cardiac death, and mortality. Hence at least 20% of patients are misclassified. A more accurate method to characterize abnormalities in cardiac conduction and repolarization, cardiac architecture, along with vascular and autonomic function is desirable and necessary. Essential to the clinical utility of this method is the identification of novel ECG patterns that are closely linked to the subsequent development of serious heart rhythm disturbances and fatal cardiac events.

Ventricular fibrillation (VF) is a disorganized and rapid rhythm of the cardiac ventricles that often leads to sudden cardiac death. Ventricular tachycardia (VT) is rapid and more organized rhythm that is also potentially fatal. Both VT and VF appear to be dependent on alterations in ventricular conduction and repolarization coupled with changes in the autonomic and vascular systems. The present invention uses high-resolution or low-resolution ECG data to identify novel ECG patterns closely linked to the subsequent development of serious heart rhythm disturbances and fatal cardiac events. The patient data derived from the ECG waveforms results in high-dimensional data. Long ECG records exhibit complex nonlinear variability that cannot be efficiently captured by traditional modeling techniques.

Two approaches are disclosed to study the dynamical and geometrical properties of ECG data. The first method uses a modified Matching Pursuit (MMP) algorithm to find a noiseless model of the ECG data that is sparse and does not assume periodicity of the signal. After the model is derived, various metrics are extracted to localize different electrical abnormalities. In the second method, space-time domain is divided into 12 regions radially from the center of mass in 12 dimensional space; the dynamical density of the ECG signal is computed, using non-Fourier or Fourier n dimensional fractional integral summation across all ECG leads on the derived MMP model (Typically the order of fractional integral could be −1.5 or −2.5 or any irrational, complex or real number), in each region and input to a genetic learning algorithm to associate them with serious heart rhythm disturbances, sudden cardiac death, other modes of death, and all-cause mortality.

SUMMARY OF THE DISCLOSURE

The claimed invention generally relates to non-invasive methods and techniques for characterizing cardiovascular systems. More specifically, the claimed invention uses surface and other electrocardiographic (ECG) data to identify and localize novel ECG patterns that have been linked to the development of serious heart rhythm disturbances, sudden cardiac death, other modes of death, and all-cause mortality.

The present disclosure evaluates the electrical activity of the heart to identify novel ECG patterns closely linked to the subsequent development of serious heart rhythm disturbances and fatal cardiac events. The present invention provides an improved and efficient method to identify and risk stratify arrhythmias of the heart using ECG data. ECG waveforms are acquired and produce high-dimensional data that can be used to identify complex nonlinear variability that is not efficiently captured by traditional techniques. Two approaches, namely model-based analysis and space-time analysis, are used to study the dynamical and geometrical properties of the ECG data. In the first a model is derived using a modified Matching Pursuit (MMP) algorithm. Various metrics and subspaces are extracted to characterize the risk for serious heart rhythm disturbances, sudden cardiac death, other modes of death, and all-cause mortality linked to different electrical abnormalities of the heart. In the second method, space-time domain is divided into a number of regions (e.g., 12 regions), the density of the ECG signal is computed in each region and input to a learning algorithm to associate them with these events. Blinded validation of the utility of these algorithms was then carried out in an independent set of patients.

BRIEF DESCRIPTION OF THE DRAWINGS

Exemplary embodiments of the present disclosure will hereinafter be described in conjunction with the following drawing figures, wherein like numerals denote like elements, and wherein:

FIG. 10 illustrates receiver-operating characteristic curves of data from the REFINE study;

FIG. 12 is a tabular summary of the results of the Sudden Cardiac Death Morphology parameter in 12 patients, stratified by randomization to atorvostatin and matching placebo;

FIG. 13 illustrates an assessment of AF severity and therapy action by Atrial Stability Risk Formula(s)

DETAILED DESCRIPTION OF THE IMPLEMENTATIONS

Figure 1:
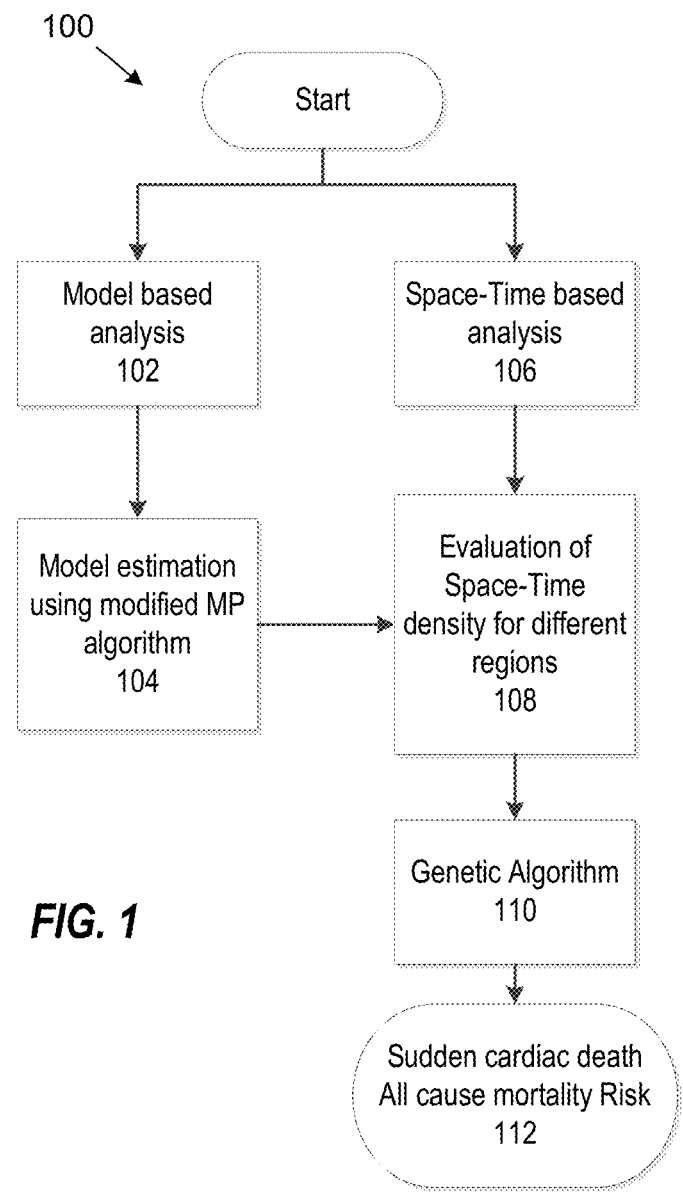
FIG. 1 shows the steps of the model-based analysis and Space-Time analysis to derive a noiseless model of the ECG data using a modified MP algorithm and linking the dynamical Space density metrics to Sudden Cardiac Death and All-Cause Mortality risk.

FIG. 1 illustrates a high-level overview of the various processes and algorithms implemented by the present disclosure to determine a sudden cardiac death or mortality risk. At 102, a model based analysis is performed. Additionally or alternatively, at 106, a space-Time based analysis may be performed at 106. At 104, a model estimation using modified MP algorithm is performed. At 108, an evaluation of Space-Time density for different regions is performed. At 110, a genetic algorithm is determined based on the output of 108. At 112, a sudden cardiac death and/or all cause mortality risk is determined. Aspects of FIG. 1 will are described in more detail below.

Figure 2:
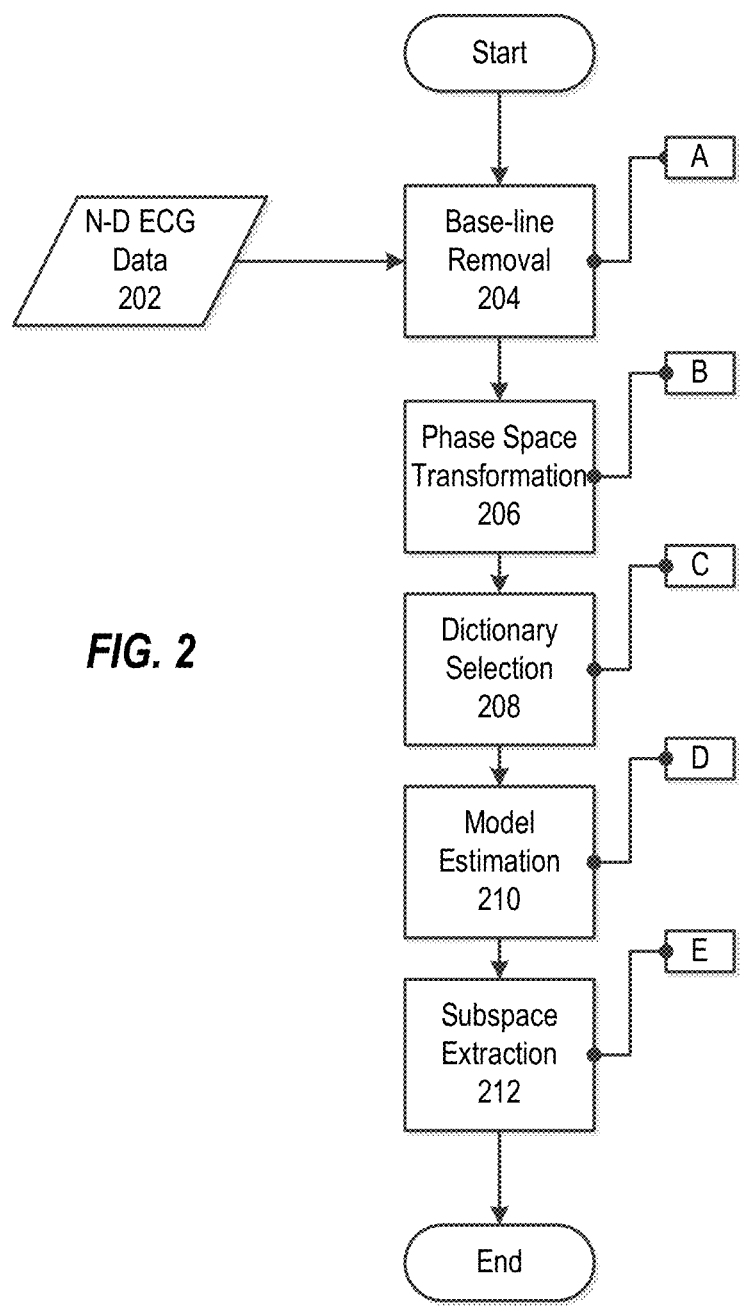
FIG. 2 shows the steps of the model-based analysis to derive a noiseless model from ECG data using a modified MP algorithm.

FIG. 2 illustrates the steps of the model-based analysis to derive a noiseless model from ECG data using an MMP algorithm. Step 204 shows the baseline removal step, step 206 represents the phase space transformation step, step 208 presents the dictionary selection step, step 210 illustrates the model estimation step and step 212 demonstrates the subspace extraction step. In FIG. 2, at 202, N-dimensional ECG is input to a modified moving average filter to remove the baseline wander from the data. The output then goes to a phase space transformation process at 206 in which a dynamically rich system (a system that can exhibit many different dynamical behaviors at different values of its parameters) is synchronized with a physiological signal, in this case ECG data, to magnify its dynamical features. For example, Rossler is a good choice as it exhibits various behaviors for different values of its parameters. The defining equations of Rossler system are as follows:

$$\begin{cases} \dot{x} = -y - z \\ \dot{y} = x + ay \\ \dot{z} = b + z(x - c) \end{cases}$$

where a, b, and c are some constants. For fixed values of a=b=0.1, Rossler system exhibits the following behavior for different values of c.

TABLE 1

| Value of c | Dynamical Behavior | Phase Space |
|---|---|---|
| c = 4 | Period-1 Orbit | FIG. 7.A |
| c = 6 | Period-2 Orbit | FIG. 7.B |
| c = 8.5 | Period-4 Orbit | FIG. 7.C |
| c = 8.7 | Period-8 Orbit | FIG. 7.D |
| c = 13 | Sparse Chaos | FIG. 7.E |
| c = 18 | Filled-in Chaos | FIG. 7.F |

Figure 3:
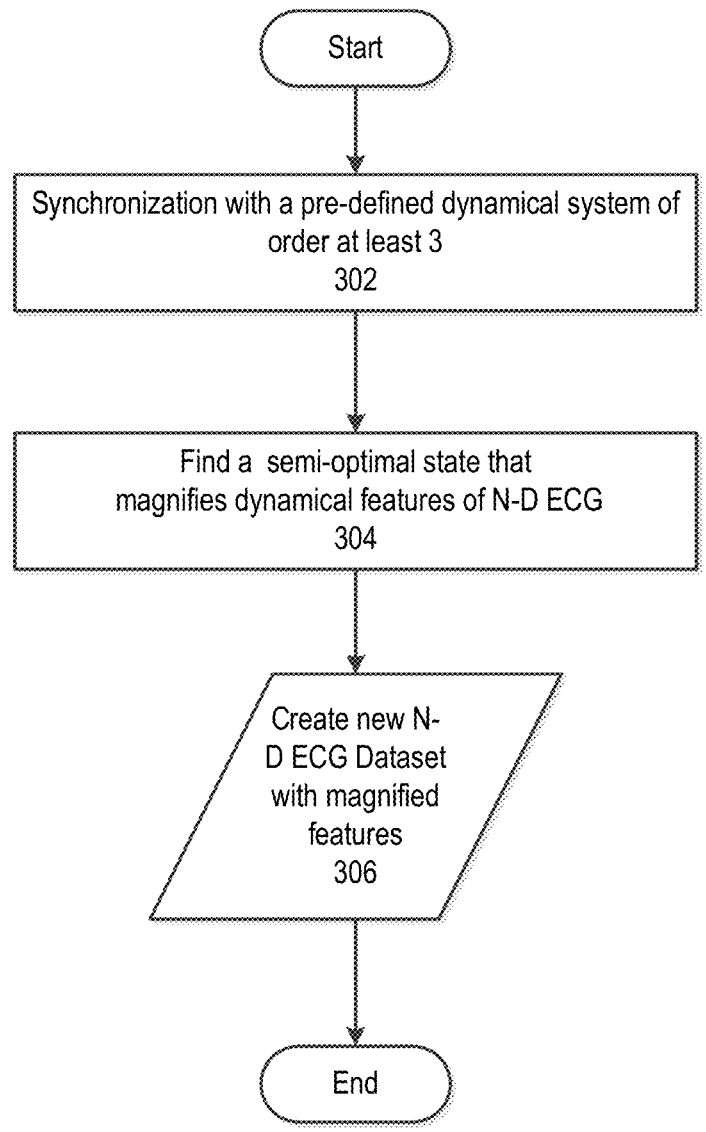
FIG. 3 presents process of phase space transformation.

The ECG data is synchronized with Rossler system and then a semi-optimal state is identified that magnifies dynamical features of the physiological signal under study, FIG. 3.

In accordance with FIG. 3, at 302, the ECG is synchronized with a dynamical system. Next, at 304, a semi-optimal state that magnifies the dynamical features of the ECG is found. This creates a new ECG dataset with magnified features at 306. Synchronization refers to phase space based synchronization of the information of the ECG system to the Rossler system. The subspaces that arise from the differences between the synchronization of these two systems are the magnifications of the dynamical features of the ECG. These subspaces comprise the new ECG dataset.

Referring again to FIG. 2, at 208, the obtained new dataset is then used to find the best dictionary(ies) that can linearly span the input. Each dictionary, $\mathcal{D}$, is a family of waveforms $\mathcal{D} = \{\phi_i | i \in 1\}$ that is used to decompose the input. Various dictionaries are now available such as Wavelet Packets, Cosine Packets, Chirplets, and so on. In accordance with some implementations, complex exponential sinusoids and Time-Frequency are used over complete dictionaries synchronized by a dynamically-rich family of post-transient Rossler trajectories.

Figure 4:
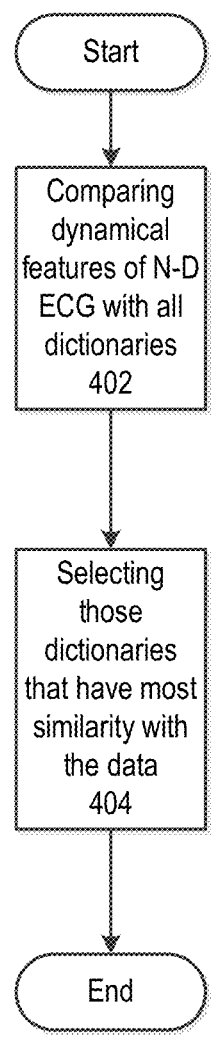
FIG. 4 illustrates the process of selecting the best dictionaries.

FIG. 4 illustrates the process of selecting the best dictionaries. At 402, different dynamical features, such as Lyapunov exponent and correlation dimension, of the ECG or other physiological signal is compared with a family of different dictionaries. At 404, those dictionaries that have most similarity to the dataset is selected to be used for model estimation, i.e. the member atoms of the selected dictionaries form the set of atoms that will be used in MMP. The dynamical features of the ECG are compared with all the dictionaries and the dictionaries are selected that have the most similarity with the data Referring again to FIG. 2, at 210, the next step is to find a sparse model (extracted from the selected dictionaries) for the physiological signal under study. For example, MMP may be used, which is an iterative process that, at each step, chooses the dictionary atom that best correlates with the signal. This process continues until a pre-defined stopping condition occurs, such as if the number of terms exceeds a threshold and/or the distance of the model and the target in the search space is smaller than a threshold. Finally, the coefficients of the selected atoms are computed.

Figure 5:
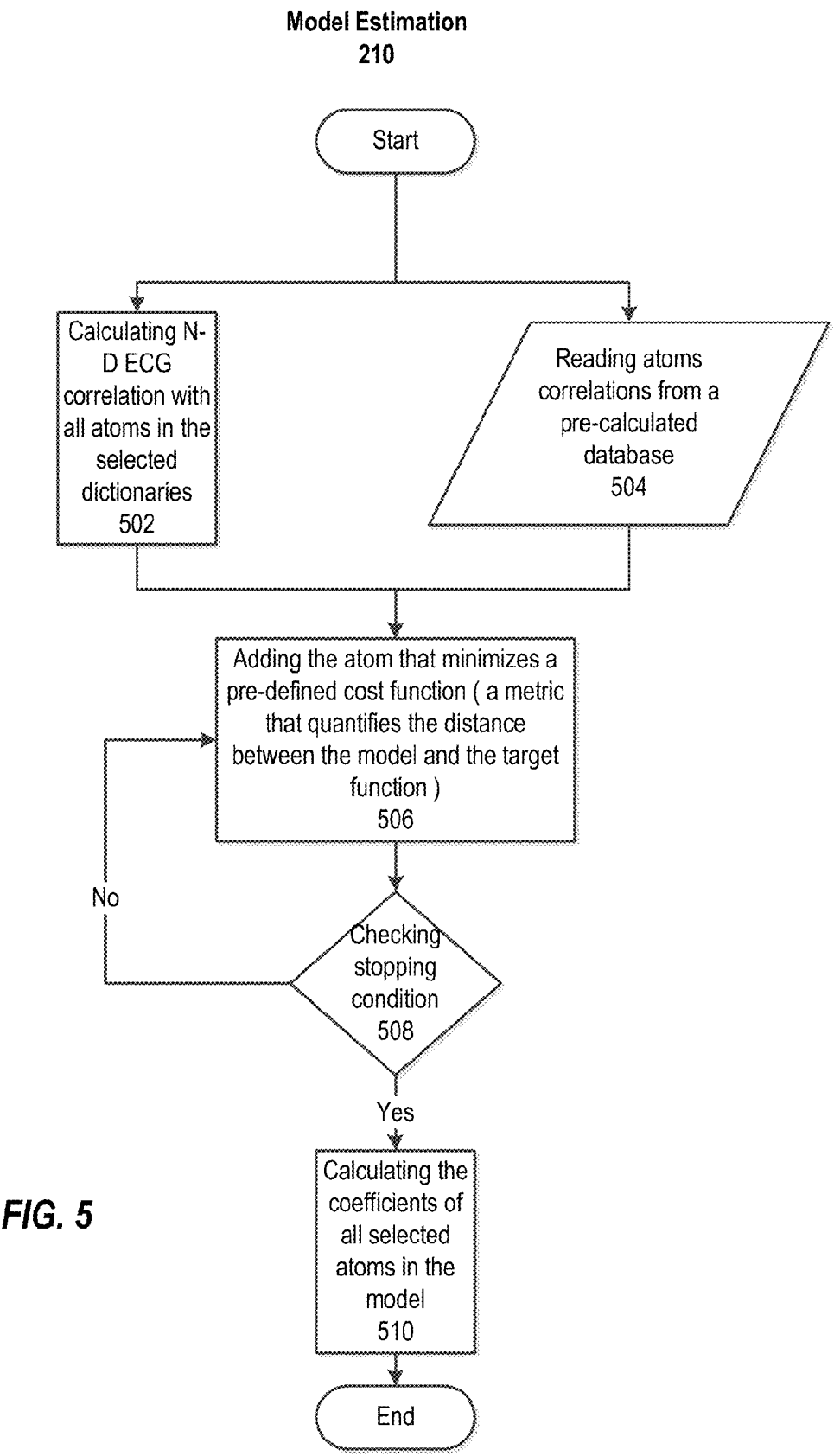
FIG. 5 sketches model estimation process where sparse linear expansion of selected atoms is used to mimic the ECG signal.
Figure 6:
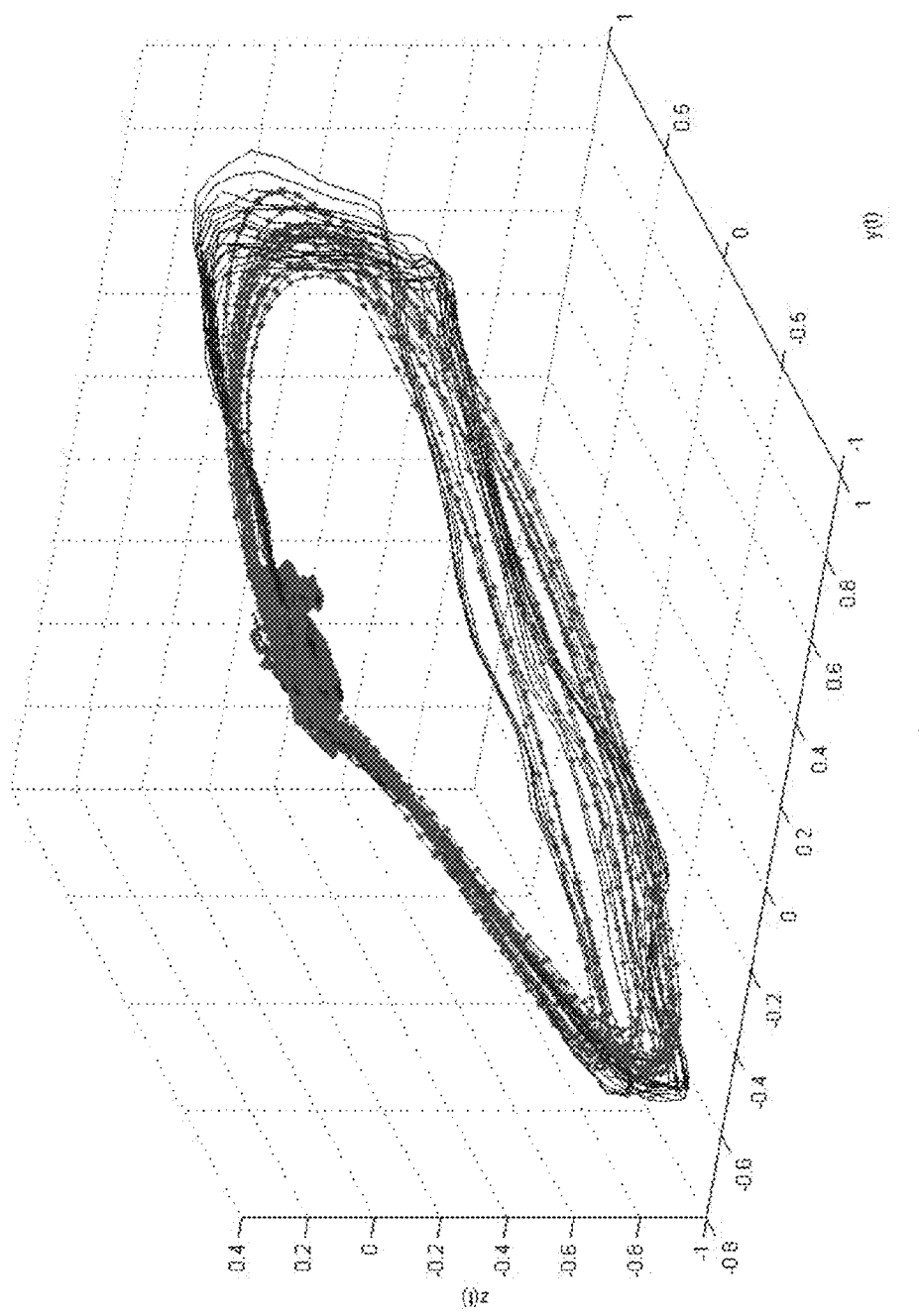
FIG. 6 illustrates blue trajectories as raw ECG signal plotted in 3-D vectorcardiographic manner, and red trajectories are the noiseless MMP model of the blue trajectories with CSF removed.
Figure 7A:
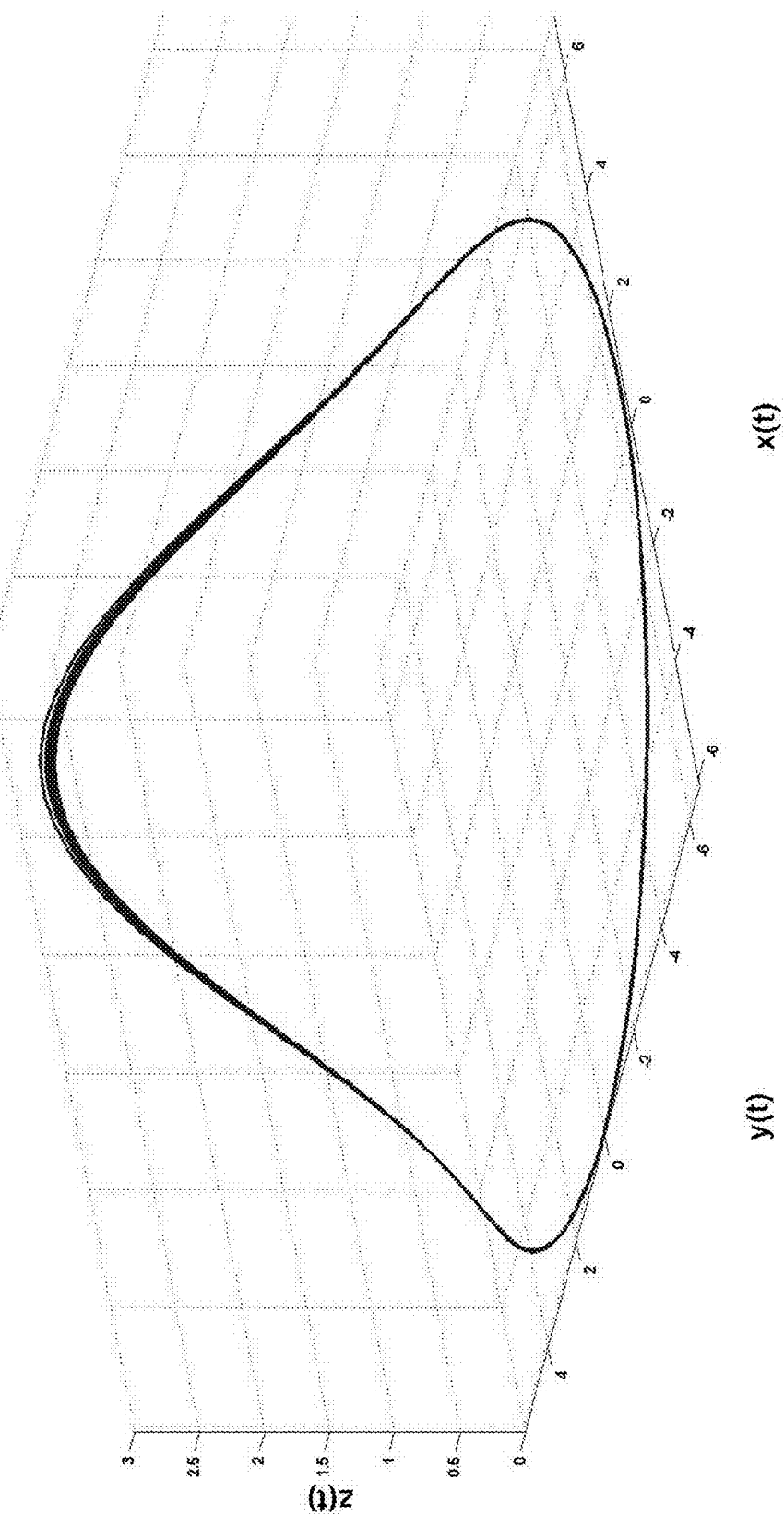
FIGS. 7A-7F present different dynamical behaviors of Rossler system for different values of its parameter, c.
Figure 7B:
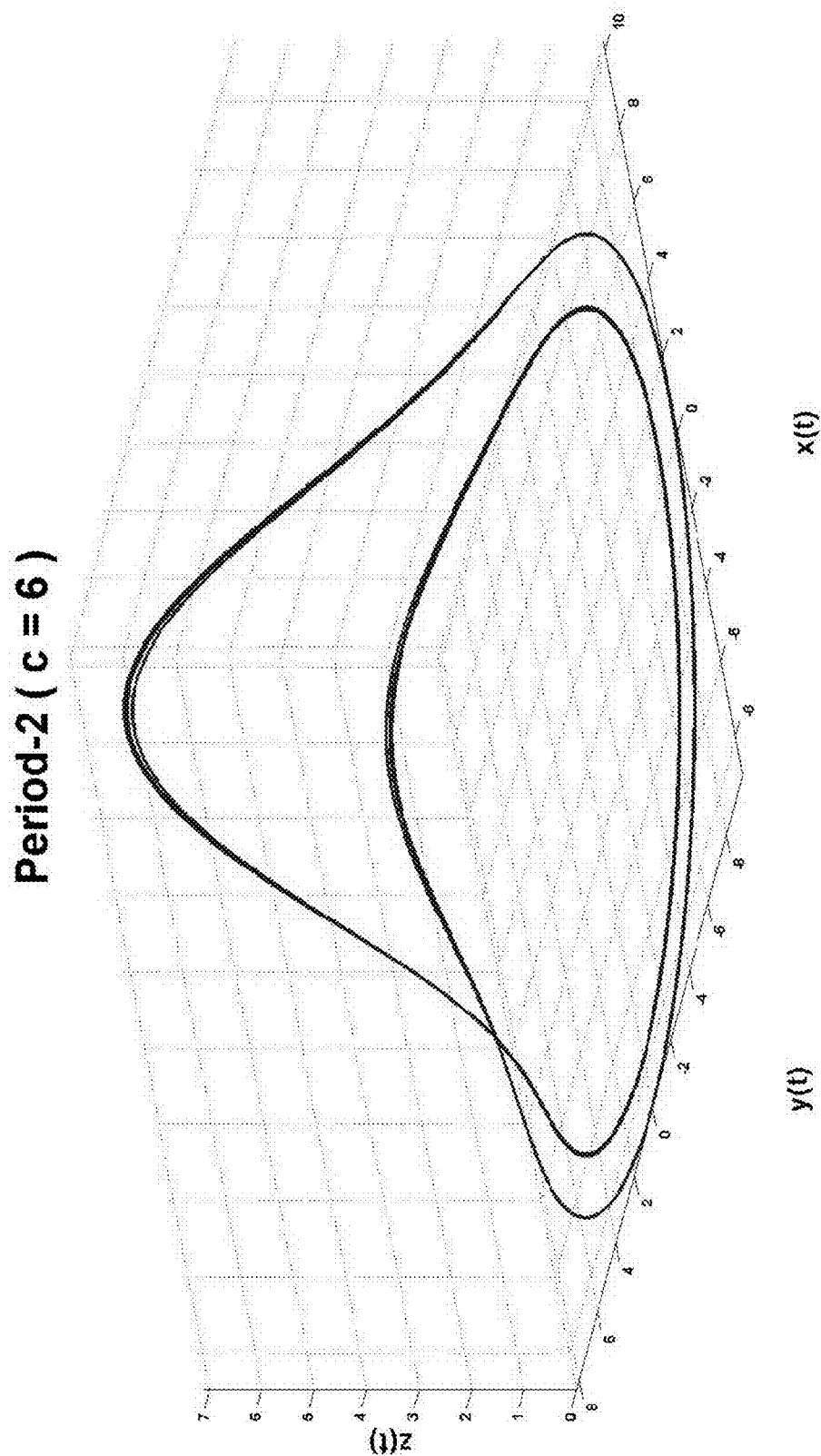
Figure 7C:
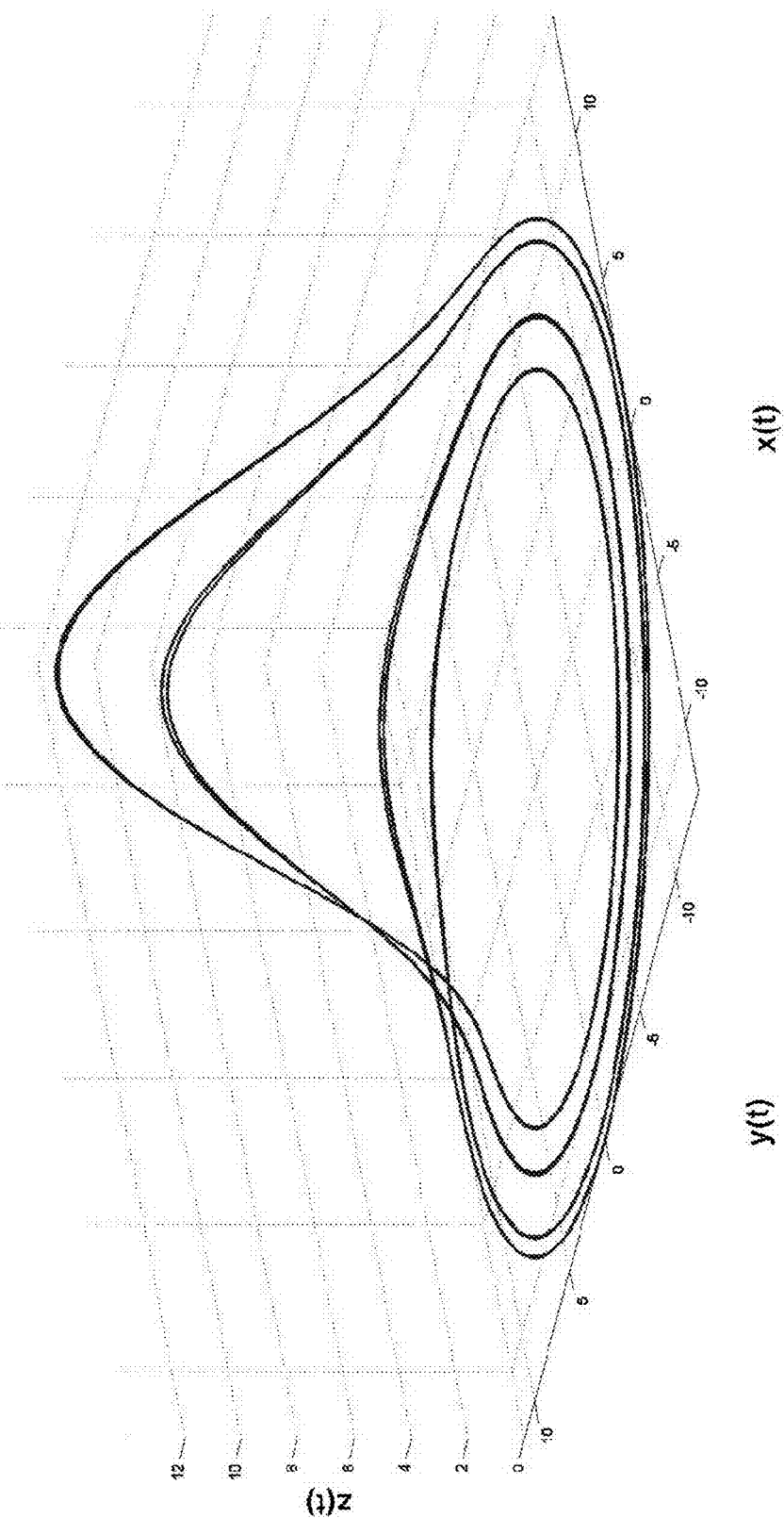
Figure 7D:
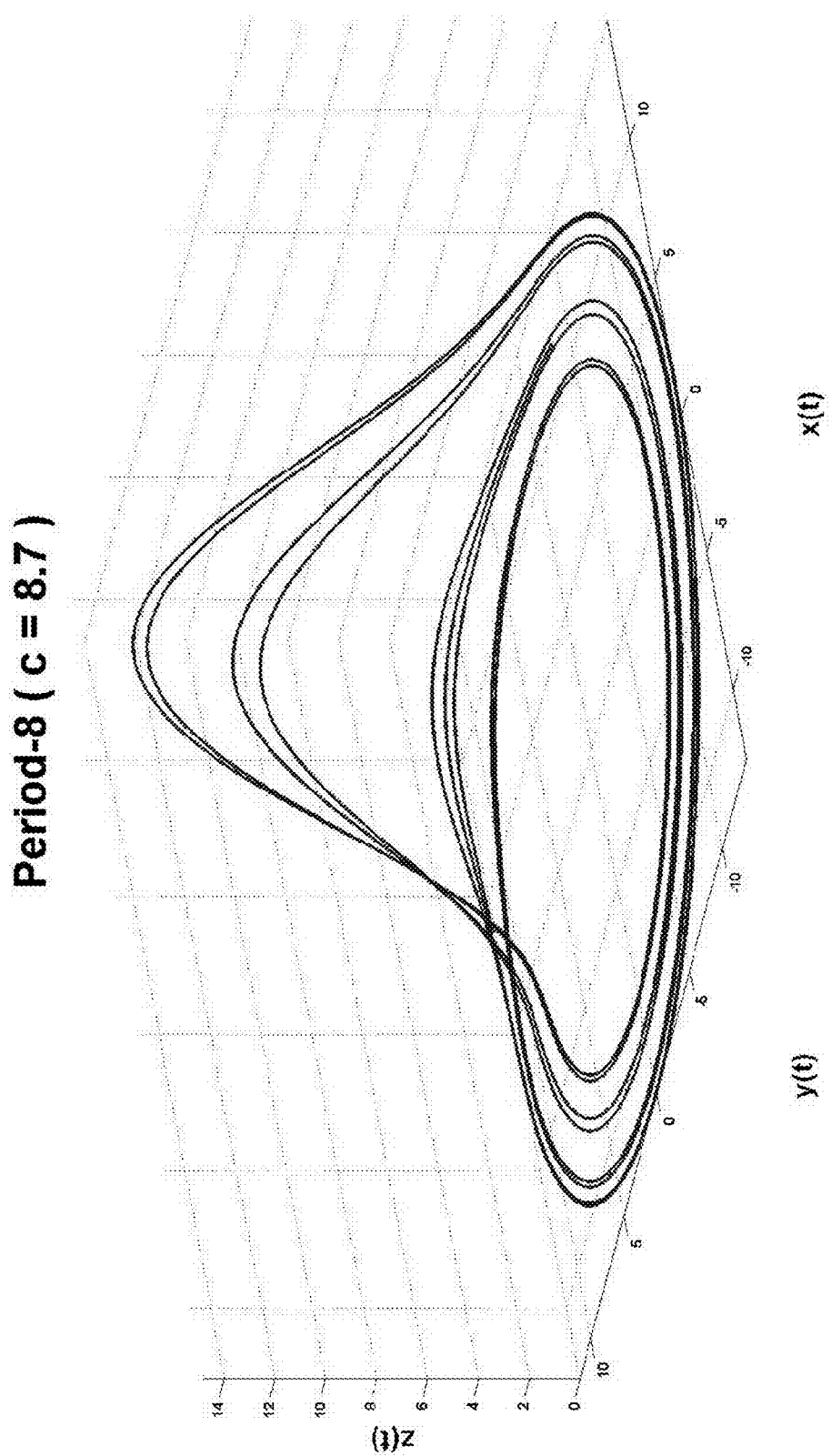
Figure 7E:
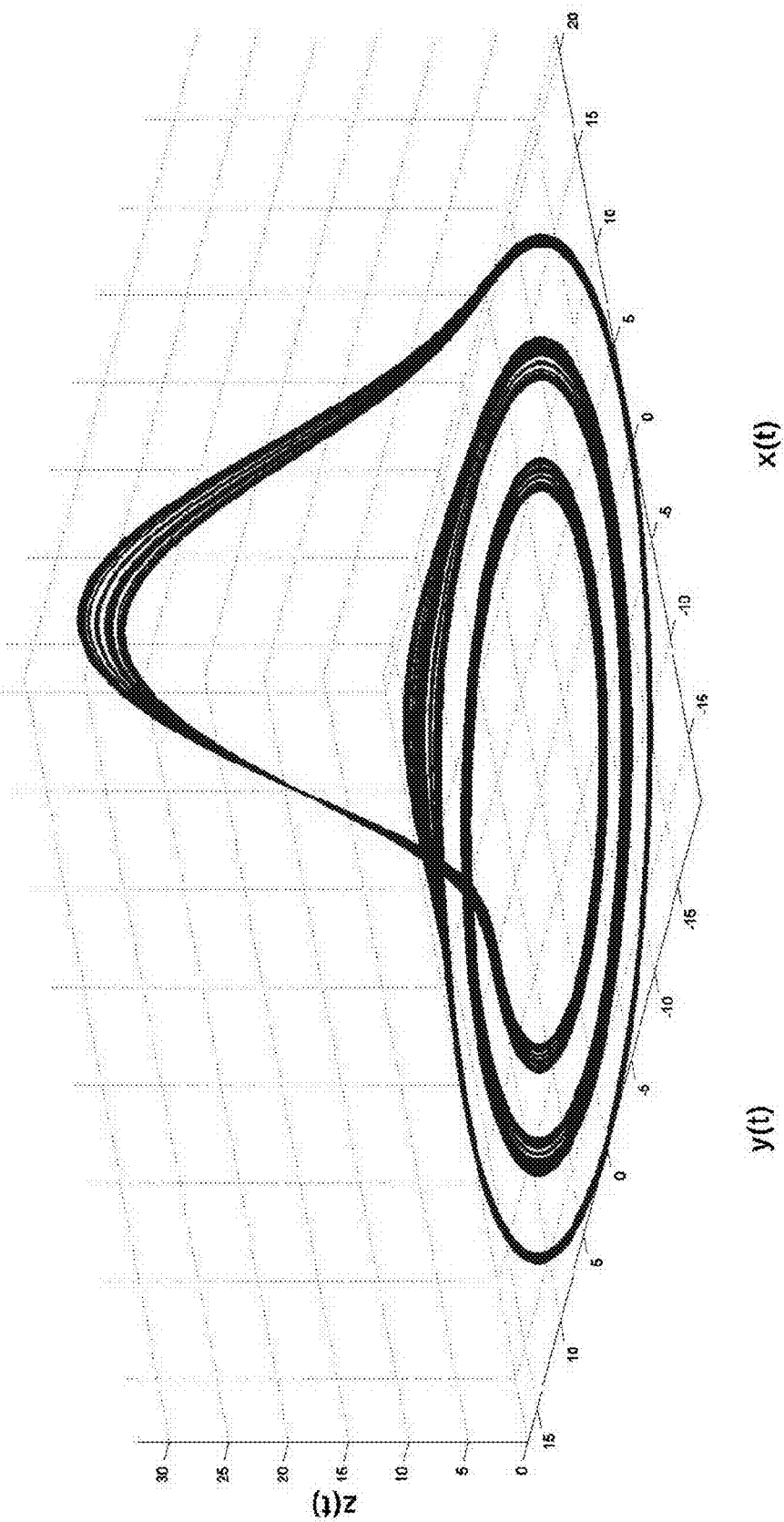
Figure 7F:
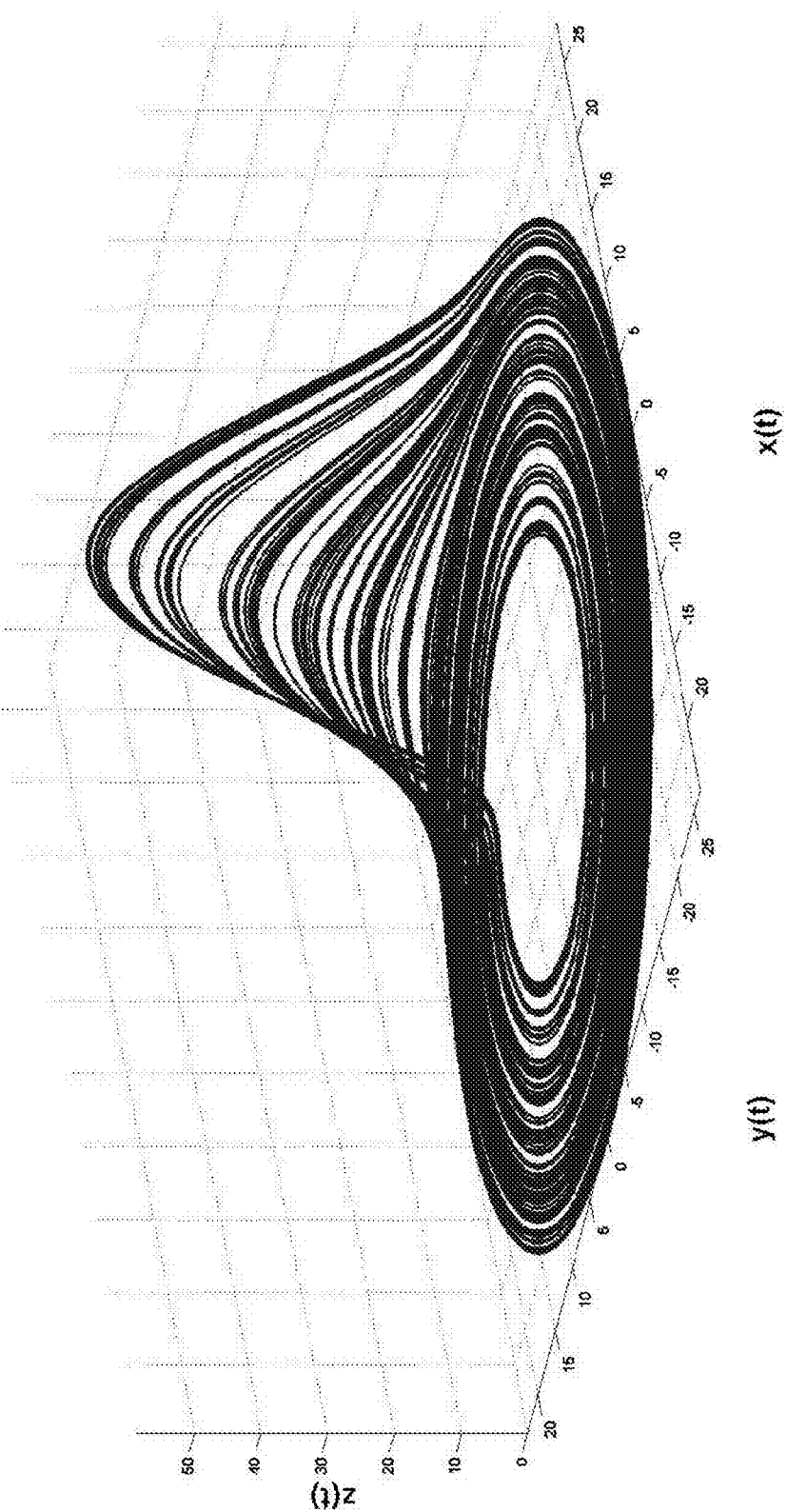
Figure 8:
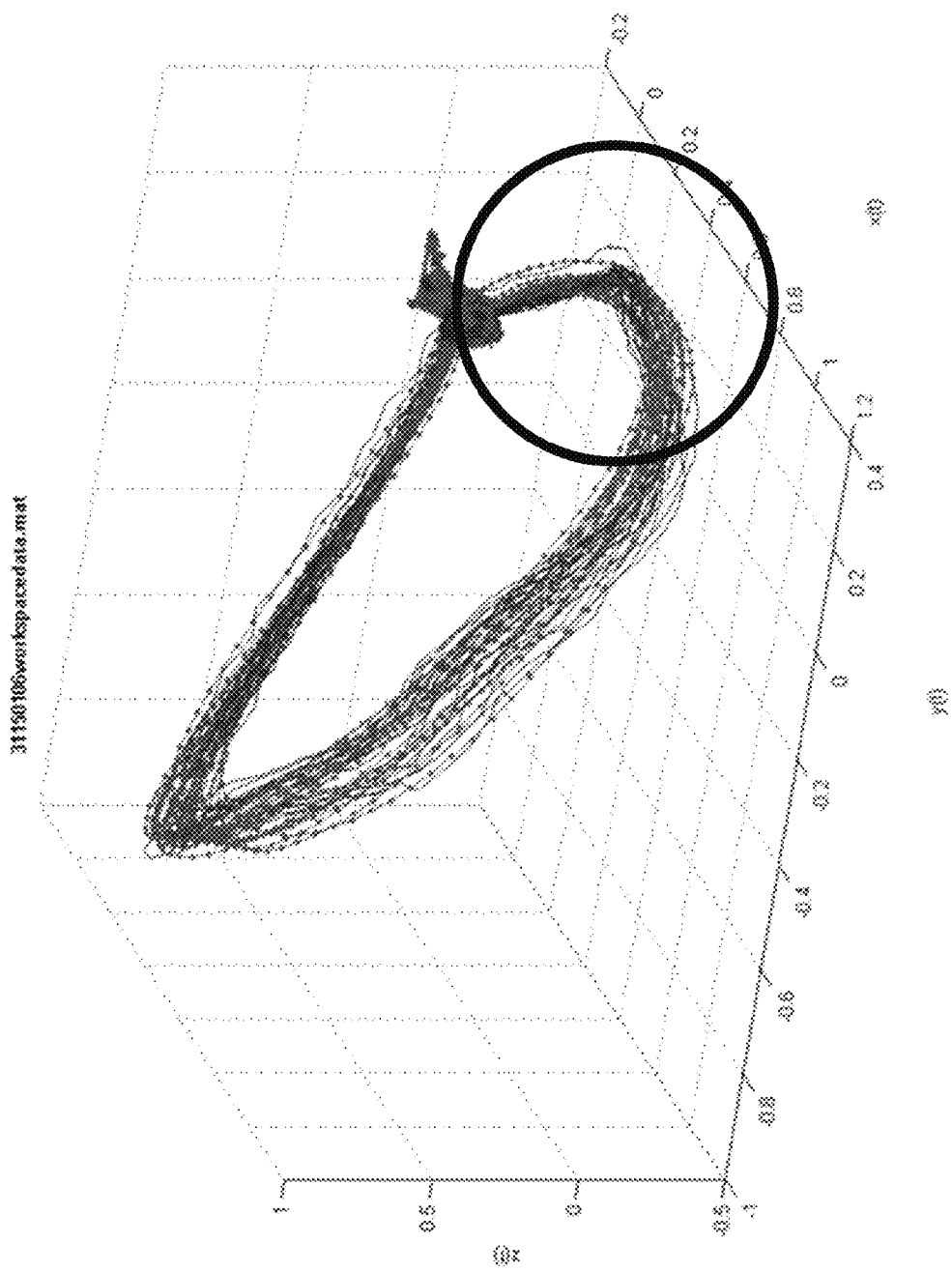
FIG. 8 presents a mathematical model derived vectorcardiogram as in FIG. 6). The departures between red and blue trajectories represent conduction delays. It is claimed that abrupt changes in impedance responsible for the generation of sub-harmonic frequencies. Scroll wave risk, with a rapid conduction delay. Notice the blue trajectories snake around the red trajectories as shown in the circled region.
Figure 9:
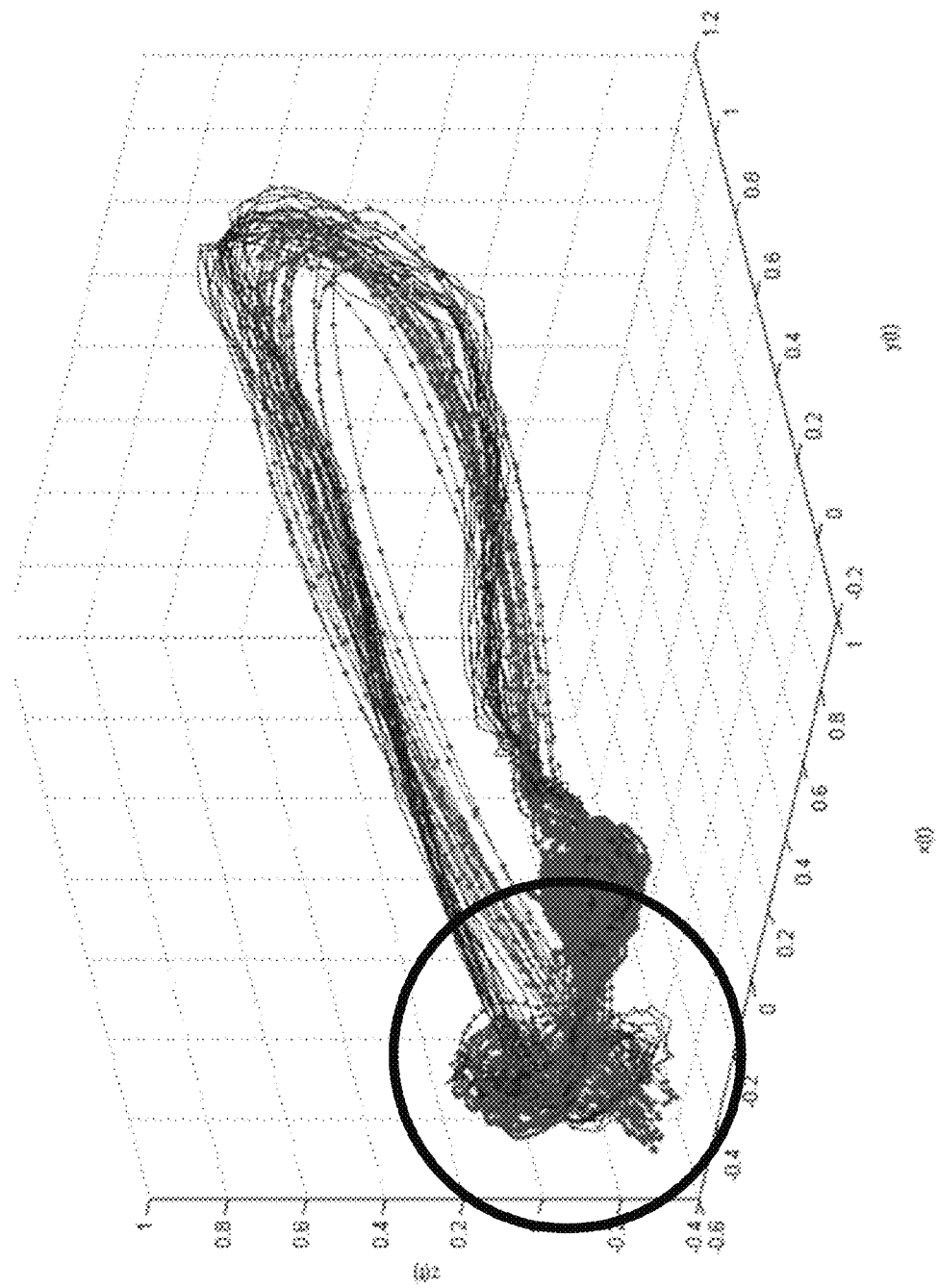
FIG. 9 presents a mathematical model derived vectorcardiogram as in FIG. 6. Vectorcardiogram of a patient after myocardial infarction who later died from sudden cardiac death. The red regions are claimed to represent arrhythmogenic potential (circled region) where a spiral wave rotates around an unexcited core.

FIG. 5 sketches the process of model estimation using MMP. At 502, the correlation of the ECG dataset with all the atoms in the selected dictionaries is computed. This information, along with the pre-evaluated cross correlation of atoms (504) is used to pick the best atom in each iteration in order to minimize a pre-defined cost function that quantifies a distance in a metric space, such as mean absolute error or mean square error, between the model and the target waveform. After the addition of each atom at 506, a stopping condition is consulted at 508 to determine whether further iterations of the algorithm are necessary. This stopping condition could take into account factors such as the number of atoms already present in the model and the fit of the model against the target waveform. If the stopping condition has been satisfied at 508, the algorithm proceeds to 510 to perform a calculation of the coefficients of the atoms. These coefficients are reclusively calculated using information captured during the iteration of the algorithm in order to optimize the fit of the model against the input waveform. The process begins with reading precomputed atom correlations and computing the correlations between the input waveform and the atoms. Atoms are iteratively added until the stopping condition is satisfied, at which point the coefficients are calculated Returning to FIG. 2, at 212, different subspaces are extracted from the derived model. Various subspaces, namely CSF trajectory, quasi-periodic and chaotic subspaces, low/high-energy subspace, and fractional derivative of the low/high-energy subspace are extracted from the derived model; however, possible subspaces that could be extracted are not limited to these examples. Each of which represents a dynamical abnormality in the tissue architecture, structure and function.

The last 20% of the selected atoms are used to form a "low energy subspace" signal corresponding to each of the leads. These low energy signals can be called x(t), y(t), and z(t) assuming 3 leads.

There are various time domain and frequency domain signal processing techniques which are being used for the analysis of ECG signals to obtain more detailed information. Time domain techniques alone are incapable of quantifying certain fluctuation characteristics of a number of pathologies related to the ECG signal. For example, with regard to the heart, traditional methods for performing frequency-domain analysis of surface ECG signals, such as the Fourier transform, are limited since they do not address the aperiodic random nature of biological and electromagnetic noise or the variation between patients. For example, in case of VT or VF, the heart generates very complex ECG waveforms that have a large variation in morphologies. Dominant frequency analysis on these ECGs can be problematic since non-linear dynamic systems can appear to generate random noise. Discrete fast Fourier transforms and wavelet analysis have been shown experimentally to be incapable of detecting deterministic chaos in the presence of strong periodicity which tends to obscure the underlying non-linear structures. Thus, the detection of complex sub-harmonic frequencies thought to exist in patients at risk for cardiac arrhythmias requires dynamic non-linear analyses. CSF are similarly thought to exist in other types of physiological signals and may be indicative of other pathophysiology not otherwise detectable from the ECG signal using prior methods.

3-D Visualization

The 3-D phase space plot localizes the presence of CSF related to structurally or electrically abnormal heart tissue. The CSF can be measured as a time delay and as a 3-D trajectory in the atrial and ventricular sub-spaces. CSF trajectory is associated with those components of the ECG that could not be captured by the dictionary, i.e. there is no linear combination of the atoms of the selected dictionaries that can represent the CSF trajectory. FIG. 7 shows a CSF removed trajectory (in red) derived from an MMP model of ECG.

The 3-D phase space plot of the present disclosure may be displayed by any type of computing device, including, but not limited to, desktop computers, workstation computers, server computers, cloud computing devices, tablet devices, smart phones, and mobile computing devices.

Altered atrial and ventricular function is linked to the development of physiological changes that could result in complex sub-harmonics and in high dimensional changes over a series of cardiac cycles. FIG. 7 illustrates one embodiment of a method whereby MMP can be used to generate 3-D vectorgram diagrams to describe the complex sub harmonics linked to structural change in the form of anisotropic propagation and localize these electrophysiological changes to correlate this with the development of serious heart rhythm disturbances, sudden cardiac death, other modes of death, and all-cause mortality.

The last 20% of the selected atoms are used to form a "low energy subspace" signal corresponding to each of the leads. These low energy signals can be called x(t), y(t), and z(t) assuming 3 leads.

It is likely that many physical phenomena can be modeled more accurately and effectively using fractional derivatives versus classical integer derivative-based models. Traditional integer order derivatives depend only on the local behavior of a function, while fractional derivatives depend also on the whole history of the function. Fractional derivatives have the unique properties of both a derivative (change) and an Integral (history). Considerable focus on fractional calculus has been simulated by the applications of this concept in different areas of physics and engineering over the last few decades. In this embodiment is a method for detecting complex beat-to-beat sub-harmonic structures in ECG and other physiological signals based on digital differentiation and integration of fractional order. Since these signals are mathematically modeled as a linear combination of the selected atoms, they can be differentiated and integrated of fractional order. Let x'(t), y'(t), and z'(t) be their integer order derivatives respectively, these derivatives and their ratios measure instability only at a local point of the signal and therefore are poor measures of stability for long complex ECG signals with significant beat to beat variability. An alternative to an integer derivative is the use of a fractional calculus to detect abnormal CSF signals in a physiological signal based on its past history.

Low-energy component subspace (made from the last 20% terms found by MMP) can be used to noiselessly find the fractional derivative of this component, since it is a linear combination of selected atoms, and this fractional derivative can be useful to distinguish patients likely versus unlikely to suffer serious heart rhythm disturbances, sudden cardiac death, other modes of death, and all-cause mortality. In addition, there are some useful fractional properties to consider. Thus suppose that x(t), y(t), and z(t) are respectively the X, Y, and Z coordinates of the low-energy component and let $x^\alpha(t)$, $y^\alpha(t)$, and $z^\alpha(t)$ be the irrational fractional derivative of order a that can be any real (or complex) number. Then the magnitude of these irrational fractional derivatives can indicate instability when large and positive. Consider the regions when the irrational fractional derivatives are positive, in such regions, the low energy reentrant wavelets have the potential to generate the arrhythmias responsible for many cases of sudden cardiac death (VT and VF) and other serious clinical events.

The magnitude of an irrational fractional derivative can be used to help highlight regions of arrhythmogenic potential in the ECG strip.

Numeric patterns of these irrational fractional derivatives relative to the conduction delays have the potential to distinguish between different arrhythmia mechanisms and modes of death.

In the second method, space-time domain is divided into a number of regions (12 or more regions) from the center of mass; the density of the baseline-removed ECG signal is computed in each region. These values contain specific information about the non-linear variability of the ECG signal that could be linked to a physiological abnormality such as abnormal calcium channel cycling. Calcium ion (Ca++) is a universal intracellular messenger. In muscle, Ca++ is best known for its role in contractile force activation. However, in recent years the critical role of Ca++ in other myocyte processes has become increasingly clear. Ca++ signaling in cardiac myocytes, as pertaining to electrophysiology (including temporal spatial action potentials and arrhythmia), is linked to excitation-force contraction coupling, modulation of contractile function due to systemic resistance (blood pressure), energy supply-demand balance (including mitochondrial function), cell death (apoptosis), and transcription regulation. It has been hypothesized that Ca++-dependent ion pump variability occurs aperiodically in pathological cardiac myocytes, this creates significant microvolt variations in the various ECG components (P, Q, R, S, T, U and other) that can be tracked and localized by linking the space-time density structures to 12 or more regions. It should be noted a simple derivative or its ratios are insufficient to characterize space-time density structures over many cardiac cycles. It has been hypothesized that Ca++-dependent ion pump variability occurs aperiodically in pathological cardiac myocytes, this creates microvolt or larger variations in ECG morphology that can be tracked and localized by linking the dynamical space density structures into 12 or more regions.

Genetic algorithms belong to class of evolutionary algorithms, which generate solutions to optimization problems using techniques inspired by the biological processes of chromosome: separation, crossover, mutation and inheritance occurring in meiosis. Alterations in the genetic code can occur via mutation and/or crossover, and are then propagated in the population via inheritance and selection. The 12 variables from the signal density become terms in an equation and these terms are selected in many different nonlinear combinations (sin, cos, cos h, sin h, Rossler functions, product, division, addition, subtraction, Gaussian, exponential functions) candidates based on the genetic operators inheritance, mutation, selection, and crossover. This generates many offspring function combinations that are evaluated and optimized by freezing all but one variable. The unfrozen variable is optimized to reduce the absolute error of the model. The other variables are optimized and frozen in sequence until all 12 terms have the lowest error. The fitness function seeks to find the solution with the lowest absolute error. This process continues until the highest-ranking solution's fitness has reached a plateau such that successive iterations no longer produce better results. These 12 quantities are input into a genetic algorithm and are modeled to link sudden cardiac death risk and all-cause mortality from the ECG data of patients that died of each cause respectively. The region decision boundaries are agnostic to clinical ECG landmarks commonly referred to as PQRST. The result is two nonlinear nested sinusoidal Gaussian equations for the heart that links the 12 dimensional dynamical space density metrics to outcome ECG data. These same ECG metrics can be used to calculate and predict the risk of serious heart rhythm disturbances, sudden cardiac death, other modes of death, and all-cause mortality.

Space-time quantities can be mapped to complex phase space differences in 12 dimensional space. Spatial changes in the phase space matrix can be extracted using a using non-Fourier or Fourier nD fractional integral summation across all ECG leads on the derived MMP model (Typically the order of fractional integral could be −1.5 or −2.5 or any irrational, complex or real number), that creates the 12 dimensional dynamical space density metrics. These metrics for the ventricle are modeled using a genetic algorithm to link nonlinear nested sinusoidal Gaussian equations with 12 independent space-time density metrics variables to associate them with serious heart rhythm disturbances, sudden cardiac death, other modes of death, and all-cause mortality.

The output of these equations is a risk metric for arrhythmias. Arrhythmogenesis in heart tissue, which is electrically and mechanical coupled excitable media, requires mathematical stability analysis for risk assessment. The occurrence of critical chaotic instabilities can be anticipated as future events by using stability analysis that reveals the generation and destruction of intermittent chaotic states. These unstable states increase the signal density in high dimensional space resulting in a strengthening of the strange attractor that can be linked to a pathological process intrinsic and extrinsic to the heart. The dynamical signal density in 12 dimensional space or higher is used to create 10 or more non-linear phase space cluster clouds. Computation for phase space dynamical signal densities can be reduced by using 3-D instead of 12 dimensional space in constrained CPU environments like mobile computers. These cluster clouds are agnostic to the traditional ECG landmarks. The moment center is computed for the normalized three or higher dimensional ECG manifold. Dynamical cloud signal densities (SD) are a mixture of Gaussian sinusoidal functions that radiate from the moment center to the outer boundary of the manifold. This allows for mixtures of Integrals of Gaussian sinusoidal and hyperbolic cosine distributions to form complex decision boundaries that can be used to predict the risk for adverse clinical outcomes as shown in the following equations. It is explicitly noted that the formulas below are being provided solely as examples, and should not be construed as limiting the disclosure, as recited in the claims, as variations, modifications, and adaptations of the equations below to achieve the functions of the present disclosure are considered to be within the scope of the appended claims.

$$\begin{aligned}\text{Risk of sudden cardiac death}=&(4+6*\text{gauss}((12100-\\&82170*SD1)/(SD2+\sin h(43.48*SD3*\text{gauss}\\&(0.1611/(SD4*\text{gauss}(SD5))+((6.172+\\&9.258*\text{gauss}(SD6/\cos h(709*\text{gauss}(-\\&2.163*SD7^2/SD8))))/\cos h(\text{gauss}(SD9*\text{gauss}\\&(SD10/SD10)))+4.054*\text{gauss}(1.954*((6.172+\\&9.258*\text{gauss}(SD6/\cos h(709*\text{gauss}(-\\&2.163*SD7^2/SD8))))/\cos h(\text{gauss}(SD9*\text{gauss}\\&(SD10/SD10))))-11.82))*\text{gauss}\\&(SD12*SDCSF1^2*SDCSF2/(SD2+\\&SDCSF3*SDCSF4))^2))-4*\text{gauss}(SDCSF2*\sin\\&h(43.48*SD3*\text{gauss}(0.1611/(SD4*\text{gauss}\\&(SD5)))+((6.172+9.258*\text{gauss}(SD6/\cos\\&h(709*\text{gauss}(-2.163*SD7^2/SD8))))/\cos h(\text{gauss}\\&(SD9*\text{gauss}(SD10/SD10)))+4.054*\text{gauss}(1.954*\\&((6.172+9.258*\text{gauss}(SD6/\cos h(709*\text{gauss}(-\\&2.163*SD7^2/SD8))))/\cos h(\text{gauss}(SD9*\text{gauss}\\&(SD10/SD10))))-11.82))*\text{gauss}\\&(SD12*SDCSF1^2*SDCSF2/(SD2+\\&SDCSF3*SDCSF4)))*\cos h(SDCSF5)*\sin h(\sin\end{aligned}$$

$h(\sin h(43.48*SD3*\text{gauss}(0.1611/(SD4*\text{gauss}$
$(SD5)))+((6.172+9.258*\text{gauss}(SD6/\cos$
$h(709*\text{gauss}(-2.163*SD7^2/SD8))))/\cos h(\text{gauss}$
$(SD9*\text{gauss}(SD10/SD10)))+4.054*\text{gauss}(1.954*$
$((6.172+9.258*\text{gauss}(SD6/\cos h(709*\text{gauss}(-$
$2.163*SD7^2/SD8))))/\cos h(\text{gauss}(SD9*\text{gauss}$
$(SD10/SD10)))-11.82))*\text{gauss}$
$(SD12*SDCSF1^2*SDCSF2/(SD2+$
$SDCSF3*SDCSF4))))))+SDCSF6*\text{gauss}$
$(SDCSF7+SDCSF1-4.834)+SDCS7*\text{gauss}$
$(0.9287+0.1436*SDCSF7^2+$
$0.1436*SDCSF1^2-0.596*SDCSF7-$
$0.596*SDCSF1))*\text{gauss}$
$((SDCSF8*SDCSF8*SDCSF9*SDCSF2-$
$0.5097*SDCSF8*SDCSF10)/SDCSF11)$ RISK of all cause mortality=$f\text{gauss}(c1*\cos(SD10+$
$SD9+SD8)+\text{gauss}(c2*SD10-c2*\cos h(c4-SD7-$
$SD2*\text{gauss}(SD1))))$     Equation 1 & 2

SD=cloud space-time signal density
SDCSF=cloud space-time signal density complex-sub-harmonic-frequency
c=real number constants Ventricular arrhythmia is a metric that gauges the risk of sustained VT and other more serious rhythms that have the potential to produce spontaneous initiation of a serious arrhythmia. Other metrics gauge the risks of various modes of death and all-cause mortality.

Figure 14:
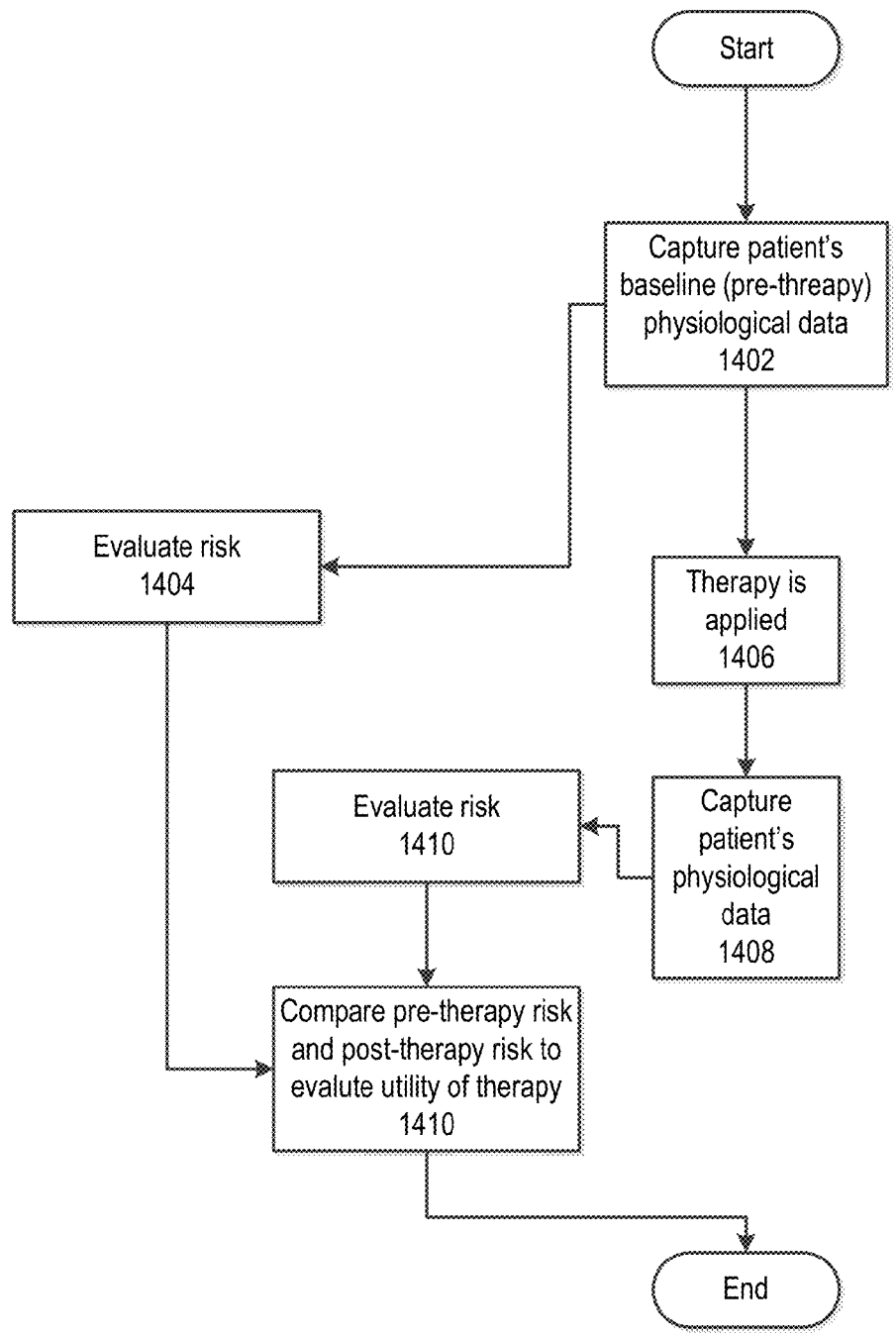
FIG. 14 is a workflow for assessing the effects (positive and negative) of various interventions that include medications, toxins, chemotherapeutic agents, surgical procedures, and other interventional procedures such as ablation, pacing, shocks and electrical therapies, and genetic therapies.

The methods described can also be used to assess therapeutic effectiveness as illustrated by the following data and workflow, as shown in FIG. 14. FIG. 14 illustrates a workflow for assessing the effects (positive and negative) of various interventions that include medications, toxins, chemotherapeutic agents, surgical procedures, and other interventional procedures such as ablation, pacing, shocks and electrical therapies, and genetic therapies. At 1402, a baseline measurement is captured before any therapy is applied and the associated risk is computed at 1404. At 1406, therapy is then applied and the patient's physiological is captured again at 1408. The risk is then computed at 14140 against the second measurement and the two risk scores are compared at 1410 to determine the utility of the therapy.

Since statins are known to reduce the risk of sudden cardiac death the effect of atorvastatin versus placebo on one of the risk assessment parameters, morphology score, was assessed. As demonstrated in the REFINE cohort analysis (FIG. 10), lower scores indicate a lower risk of sudden cardiac death. The group of patients included in this analysis had hypertrophic cardiomyopathy and were randomized to receive atorvastatin 40 mg daily or matching placebo for 12 months.

Figure 11:
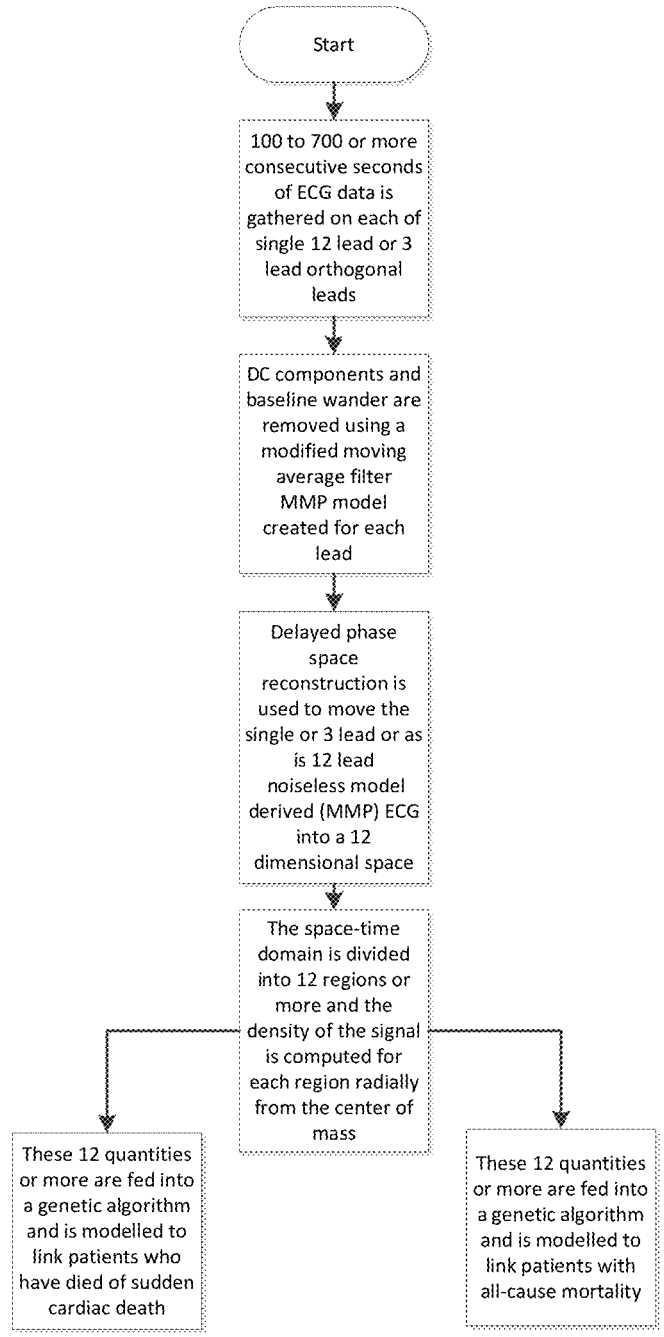
FIG. 11 shows the steps of the model-based analysis to derive a noiseless model from ECG data using a modified MP algorithm and linking this to Space-time densities with can be used to create risk metrics for adverse clinical events.

FIG. 10 illustrates receiver-operating characteristic curves of data from the REFINE study (Exner et al., Journal of the American College of Cardiology 2007; 50:2275-84). Upper panel provides the receiver operating characteristic curve (ROC) for the combination of traditional ECG parameters shown to be optimal in that study in predicting the primary outcome of cardiac death or non-fatal cardiac arrest. The lower panel shows the results for the proposed method to identify patients at risk of this same outcome. The area under the ROC curve is significantly larger (p=0.006) for the proposed method (lower panel) as compared to the prior approach (upper panel) when the upper 45 patients characterized at risk using the proposed method is compared to the 45 patients with an ejection fraction under 50% plus impaired heart rate turbulence and abnormal T wave alternans. Moreover, the proposed method results in augmented positive as well as negative predictive accuracy;

FIG. 11 Shows the steps of the model-based analysis to derive a noiseless model from ECG data using a modified MP algorithm and linking this to Space-time densities with can be used to create risk metrics for adverse clinical events. The ECG data is collected and modeled using MMP, followed by a transformation in 12 dimensional space. The space in then divided in 12 or more regions and the signal density is computed in each region. Finally, the 12 or more signal densities are inputted into a genetic algorithm to link the patients who died of sudden death to their corresponding signals densities. This linking is repeated for patients whose death was classified as all-cause.

As shown, morphology scores significantly improved over time in the atorvastatin-treated patents, but did not change in the patients who were randomly assigned to placebo (FIG. 12). The disclosed methods are applied to generate formulas to assess risk for atrial arrhythmia, such as AF. FIG. 13 shows the atrial risk score of a patient diagnosed with AF, while on the standard of care treatment, and when off the standard of care treatment. The risk score changes by a factor of 10, indicating this risk score is tracking a) the severity of the AF, and b) the effectiveness of the drug regimen being used to treat the patient. Assessing atrial risk while in sinus rhythm is poorly understood. It is hypothesized that proximal AF is driven by low energy reentrant circuits are insufficient to activate AF continuously. These low energy signals can be detected and quantified using space density metrics described above (see below for exemplar atrial risk formula). These two examples provides evidence that favorable drug effects can be identified using the disclosed methods.

Atrial Risk Score=$4+6*\text{gauss}((12100-82170*SD1)/$
$(SD2+\sin h(43.48*SD3*\text{gauss}(0.1611/$
$(5D4*\text{gauss}(SD5)))+((6.172+9.258*\text{gauss}(SD6/$
$\cos h(709*\text{gauss}(-2.163*SD12^2/SD1))))/\cos$
$h(\text{gauss}(SD2*\text{gauss}(SD3/SD4)))+4.054*\text{gauss}$
$(1.954*((6.172+9.258*\text{gauss}(SD6/\cos$
$h(709*\text{gauss}(-2.163*SD12^2/SD1))))/\cos$
$h(\text{gauss}(SD2*\text{gauss}(SD3/SD4))))-11.82))*\text{gauss}$
$(SD5*SD6^2*SD12/(SD2+SD1*SD2)))^2))-$
$4*\text{gauss}(SD12*\sin h(43.48*SD3*\text{gauss}(0.1611/$
$(SD4*\text{gauss}(SD5)))+((6.172+9.258*\text{gauss}(SD6/$
$\cos h(709*\text{gauss}(-2.163*SD12^2/SD1))))/\cos$
$h(\text{gauss}(SD2*\text{gauss}(SD3/SD4)))+4.054*\text{gauss}$
$(1.954*((6.172+9.258*\text{gauss}(SD6/\cos$
$h(709*\text{gauss}(-2.163*SD12^2/SD1))))/\cos$
$h(\text{gauss}(SD2*\text{gauss}(SD3/SD4))))-11.82))*\text{gauss}$
$(SD5*SD6^2*SD12/(SD2+SD1*SD2)))*\cos$
$h(\text{gauss1}Vz(8))*\sin h(\sin h(\sin$
$h(43.48*SD3*\text{gauss}(0.1611/(SD4*\text{gauss}$
$(SD5)))+((6.172+9.258*\text{gauss}(SD6/\cos$
$h(709*\text{gauss}(-2.163*SD12^2/SD1))))/\cos$
$h(\text{gauss}(SD2*\text{gauss}(SD3/SD4)))+4.054*\text{gauss}$
$(1.954*((6.172+9.258*\text{gauss}(SD6/\cos$
$h(709*\text{gauss}(-2.163*SD12^2/SD1))))/\cos$
$h(\text{gauss}(SD2*\text{gauss}(SD3/SD4))))-11.82))*\text{gauss}$
$(SD5*SD6^2*SD12/(SD2+SD1*SD2))))))$

Having thus described several embodiments of the claimed invention, it will be rather apparent to those skilled in the art that the foregoing detailed disclosure is intended to be presented by way of example only, and is not limiting. Many advantages for non-invasive method and system for location of an abnormality in a heart have been discussed herein. Various alterations, improvements, and modifications will occur and are intended to those skilled in the art, though not expressly stated herein. Any alterations, improvements, and modifications are intended to be suggested hereby, and are within the spirit and the scope of the claimed invention. Additionally, the recited order of the processing elements or sequences, or the use of numbers, letters, or other designations therefore, is not intended to limit the claimed processes to any order except as may be specified in the claims. Accordingly, the claimed invention is limited only by the following claims and equivalents thereto.

What is claimed is:

1. A method for quantifying the risk of serious arrhythmias, sudden cardiac death, or other modes of death and all-cause mortality events in mammals, comprising:
   obtaining ECG data, the ECG data comprising at least one heart beat cycle;
   processing the ECG data to detect patterns that predict a risk of sudden cardiac death, other modes of death, and all-cause mortality, the processing being performed without the use of data from other measuring devices or invasive procedures, the ECG data including at least 12 dimensional dynamical phase space densities, the processing including using a time interval to quantify the risk of sudden cardiac death, other modes of death, and all-cause mortality; and
   creating a 3-D phase space plot from processed ECG data, the 3-D phase space plot visualization providing a visual indication of regions of a heart that include abnormal heart tissue,
   wherein the at least one heart beat cycle corresponds to a vector sum electrical activation pathway through the heart, and
   wherein the vector sum electrical activation pathway is used with time information associated with the at least 12 dimensional dynamical space density to determine the risk of sudden cardiac death, other modes of death and all-cause mortality.

2. The method of claim 1, wherein the predetermined time interval is at least 50 seconds and typically from 100 to 700 seconds.

3. The method of claim 1, further comprising using at least 12 variables corresponding to the at least 12 dimensional dynamical space density as terms that are selected in nonlinear combinations selected from a list comprising sin, cos, cos h, sin h, Rossler functions, product, division, addition, subtraction, Gaussian, exponential functions and become candidates based on the genetic operators selected from a second list comprising inheritance, mutation, selection, and crossover.

4. The method of claim 3 further comprising:
   generating offspring function combinations that are evaluated and optimized by freezing all but one variable;
   optimizing an unfrozen variable to reduce an absolute error of a model;
   optimizing in a sequence, the other variables until all at least 12 variable have a lowest error;
   using a fitness function to determine a solution having a lowest absolute error; and
   continuing until a highest-ranking solution's fitness has reached a plateau such that successive iterations no longer produce better results.

5. The method of claim 4, further comprising:
   using the at least 12 variables in a genetic algorithm; and
   modeling, using the at least 12 variables to link sudden cardiac death risk, other modes of death and all-cause mortality to the ECG.

6. The method of claim 3, wherein the at least 12 dimensional phase space information from the heart can be machine learned based on mining and linking of the ECG data to associated patient outcomes.

7. The method of claim 6, further comprising associating other biomarkers to the at least 12 dimensional phase space information.

8. The method of claim 7, further comprising associating an effectiveness of patient therapies that includes using the model results to guide a treatment or intervention.

9. The method of claim 1, further comprising substituting other physiological data for the ECG data, the other physiological data comprising one of blood pressure and pulse oximetry.

10. A method for displaying risk of cardiovascular or all-cause mortality event in a mammalian heart, comprising:
    obtaining ECG data for the heart, the ECG data comprising at least one heart beat cycle;
    processing the ECG data to detect an abnormality in the heart and the risk for sudden cardiac death (SCD) and all-cause mortality without use of other measuring devices or invasive procedures; and
    using phase information to determine a location of the abnormality to visually display the potential to be arrhythmogenic,
    wherein the abnormality in the heart is detected within a time interval of between 50 seconds and 700 seconds,
    wherein the heart beat cycle corresponds to a vector sum electrical activation pathway through the heart, and the pathway is used with at least 12 dimensional dynamical space density time information to determine the risk of sudden cardiac death and all-cause mortality.

11. The method of claim 10, the step of processing the ECG data comprising creating an at least 12 dimensional phase space diagram from the ECG data, and using the at least 12 dimensional phase space diagram to detect the risk of sudden cardiac death and all-cause mortality.

12. The method of claim 11, further comprising modeling the at least 12 dimensional phase space information on a reconstructed 3D model of the heart to visually display where the abnormality is located in the heart and to display a potential of the abnormality to be arrhythmogenic.

13. The method of claim 10, further comprising using at least 12 variables corresponding to the at least 12 dimensional dynamical space density as terms that are selected in nonlinear combinations selected from a list comprising sin, cos, cos h, sin h, Rossler functions, product, division, addition, subtraction, Gaussian, exponential functions and become candidates based on the genetic operators selected from a second list comprising inheritance, mutation, selection, and crossover.

14. The method of claim 13, further comprising:
    generating offspring function combinations that are evaluated and optimized by freezing all but one variable;
    optimizing an unfrozen variable to reduce an absolute error of a model;
    optimizing in a sequence, the other variables until all at least 12 variable have a lowest error;
    using a fitness function to determine a solution having a lowest absolute error; and
    continuing until a highest-ranking solution's fitness has reached a plateau such that successive iterations no longer produce better results.

15. The method of claim 13, further comprising:
    using the at least 12 variables in a genetic algorithm; and
    modeling, using the at least 12 variables, to link sudden cardiac death risk, other modes of death and all-cause mortality to the ECG.

16. The method of claim 13, wherein the at least 12 dimensional phase space information from the heart can be machine learned based on mining and linking of the ECG data to associated patient outcomes.

17. The method of claim 10, further comprising associating other biomarkers to the at least 12 dimensional phase space information.

18. The method of claim 17, further comprising associating an effectiveness of patient therapies that includes using the model results to guide a treatment or intervention.

19. The method of claim 10, further comprising extracting measures of cardiac output including ejection fraction by mining and linking ECG data to associated patient measures of ejection fraction based on other cardiac imaging modalities.

* * * * *